United States Patent [19]

Schoengen et al.

[11] 4,302,595

[45] Nov. 24, 1981

[54] PROCESS FOR THE PREPARATION OF TEREPHTHALIC ACID BY THE HYDROLYSIS OF INTERMEDIATE STAGE CRUDE DIMETHYL TEREPHTHALATE

[75] Inventors: Anton Schoengen, Witten; Georg Schreiber, Cologne; Heinz Schroeder, Witten, all of Fed. Rep. of Germany

[73] Assignee: Dynamit Nobel Aktiengesellschaft, Troisdorf, Fed. Rep. of Germany

[21] Appl. No.: 79,253

[22] Filed: Sep. 27, 1979

[30] Foreign Application Priority Data

Apr. 21, 1979 [DE] Fed. Rep. of Germany ....... 2916197

[51] Int. Cl.$^3$ .............................................. C07C 51/09
[52] U.S. Cl. ...................................... 562/483; 203/73
[58] Field of Search ................. 562/483, 485; 203/73, 203/DIG. 6; 560/78

[56] References Cited

U.S. PATENT DOCUMENTS

| | | | |
|---|---|---|---|
| 2,992,168 | 7/1961 | Wilson et al. | 560/78 |
| 3,108,132 | 10/1963 | McKinney | 560/78 |
| 3,396,087 | 8/1968 | Claybaugh et al. | 560/78 |
| 3,594,414 | 7/1971 | Katzschmann | 562/483 |
| 4,118,313 | 10/1978 | Hadamovsky et al. | 560/78 |

FOREIGN PATENT DOCUMENTS

| | | |
|---|---|---|
| 1299627 | 7/1969 | Fed. Rep. of Germany . |
| 1130695 | 4/1966 | United Kingdom . |
| 1344383 | 1/1974 | United Kingdom . |

OTHER PUBLICATIONS

Butler, P. A. *Chemical and Process Engineering*, Oct. 1971, pp. 68–71.

*Primary Examiner*—Natalie Trousof
*Assistant Examiner*—L. Hendriksen
*Attorney, Agent, or Firm*—Craig and Antonelli

[57] ABSTRACT

In a process for the preparation of fiber-grade terephthalic acid from intermediate stage crude dimethyl terephthalate, the crude dimethyl terephthalate, which has a limited content of intermediate oxidation products including a content of terephthalaldehydic acid methyl ester of up to 0.1% by weight based on the weight of the crude dimethyl terephthalate, is hydrolyzed with water at a weight ratio of the crude dimethyl terephthalate to water of between 3:1 and 0.1:1 and at a temperature between 140° C. and 350° C. and under a pressure required to maintain a liquid phase (e.g., from 6 to 200 bars) to produce a reaction mixture containing crystalline fiber-grade terephtalic acid and thereafter the terephthalic acid is recovered from the reaction mixture. The initial crude dimethyl terephthalate used as a starting material is obtained from a crude ester mixture produced by the oxidation of p-xylene and/or methyl p-toluate with oxygen-containing gases in the presence of heavy metal-containing oxidation catalyst at an elevated temperature and under an elevated pressure and by esterification of the oxidation mixture with methanol at an elevated temperature and elevated pressure followed by separating the resulting crude ester mixture by distillation into a methyl p-toluate enriched fraction, a residual high-boiling fraction and the crude dimethyl terephthalate having the limited content of intermediate oxidation products.

8 Claims, 10 Drawing Figures

PROCESS FOR THE PREPARATION OF TEREPHTHALIC ACID BY THE HYDROLYSIS OF INTERMEDIATE STAGE CRUDE DIMETHYL TEREPHTHALATE

This invention relates to a production of terephthalic acid (TPA) and more particularly to a process for the production of a fiber-grade TPA from p-xylene (p-x) by the hydrolysis of an intermediate stage crude dimethyl terephthalate (DMT) in water at an elevated temperature and under elevated pressure.

The intermediate stage crude dimethyl terephthalate (DMT) is obtained from a crude ester mixture produced by the well known Witten or Katzschmann process, i.e. by the oxidation of p-xylene and/or methyl p-toluate (PTE) with an oxygen-containing gas in the presence of heavy metal-containing oxidation catalysts at an elevated temperature and under elevated pressure; and by esterification of the oxidation mixture with methanol at an elevated temperature and under elevated pressure; and by distillative separation of the crude ester mixture into a PTE-enriched fraction and a fraction enriched with intermediate oxidation products and other by-products, which are recycled into the oxidation stage, a residual high boiling fraction; and a crude containing DMT having a limited content of intermediate oxidation products especially terephthalaldehydic acid methyl ester (TAE) and other by-products. The terephthalic acid (TPA) is produced by continuous hydrolysis of the crude or raw DMT with water at a weight ratio of the crude DMT to water of between 3:1 and 0.1:1, and at temperature of between 140° and 350° C. and under a pressure required to maintain a liquid phase; and by recovery of the TPA from the reaction mixture.

The direct oxidation of p-xylene with atmospheric oxygen in the presence of acetic acid as a solvent, a bromine-containing activator, as well as heavy-metal-containing catalysts, leads to crude TPA as the product and, after a further purifying step and separation by multistage crystallization, leads to fiber-grade TPA, which, by direct esterification with ethylene glycol, polycondensation, and melt-spinning, results in polyester fibers, filaments, and films. Yet, it is economically advantageous to effect the production of fiber-grade TPA from p-xylene by way of hydrolysis of crude DMT in accordance with the process of this invention as described hereinbelow.

The need for such a process is due to the fact that the acetic acid solvent, in conjunction with the bromine compounds employed, cause high corrosiveness in the process of the direct oxidation of p-xylene to TPA, and is further due to the fact that losses are encountered in this process due to combustion of acetic acid and also during the distillative working-up process and recycling of the acetic acid.

The hydrolysis of a crude DMT, as obtained in the Katzschmann or Witten process according to the state of the art as described, for example, in *Chemical and Process Engineering*, October 1971, page 68, does not lead to a pure terephthalic acid, which can be processed without additional purifying steps into polyester fibers and filaments by direct esterification with ethylene glycol, poly-condensation, and melt-spinning, due to the fact that this crude DMT still contains low-boiling and high-boiling by-products.

German Pat No. 1,299,627 proposes a process for the production of fiber-grade terephthalic acid by the neutral hydrolysis of fiber-grade dimethyl terephthalate (DMT) at temperatures of 180°–280° C. under elevated pressure in corrosion-resistant vessels, wherein the hydrolysis is effected with aqueous neutral salt solutions. The terms "fiber-grade terephthalic acid" and "fiber-grade DMT" utilized in German Pat. No. 1,299,627 mean a quality which makes these products suitable for direct esterification or interesterification with ethylene glycol and further processing into polyesters for the manufacture of polyester fibers and filaments.

German Patent Application Ser. No. 16 18 503 describes a process for the production of terephthalic acid from alkyl terephthalate by reacting the alkyl terephthalate in water at a weight ratio of 1:1 under autogenous pressure at a temperature in the range from 140° to 350° C., until the hydrolysis has been essentially completed; where after the terephthalic acid is separated from the thus-produced hydrolyzate. However, the effect of the low- and high-boiling impurities in the alkyl terephthalates utilized as the hydrolysis starting material is not taken into account and, consequently, a "fiber-grade" DMT quality suitable for processing into fibers initially must be created by recrystallization of crude DMT.

German Patent Application Ser. No. 24 60 887 or U.S. Pat. No. 4,076,946 describes the removal of aldehydic impurities, especially the methyl ester of terephthalaldehydic acid (TAE) in a crude DMT fraction by catalytic hydrogenation, and a distillative removal is indicated as being very difficult because of the similarity in the boiling points of TAE and DMT. Concentrations on the order of 5,000–10,000 p.p.m. of TAE in crude DMT are described as resulting after distillation to remove the TAE with the methyl p-toluate fraction. Consequently, crystallization of the crude DMT is mentioned as a possible procedure for removing the TAE.

TAE is converted into terephthalaldehydic acid (TAA) during the hydrolysis of crude DMT and is then present with a content corresponding to the TAE content in addition to the thus-formed terephthalic acid (TPA) and the other by-products. TAA precipitates together with TPA, and there occurs an incorporation of TAA into the TPA crystal lattice. Since TAA is an impurity which is disadvantageous for the further processing of TPA into polyesters for filaments and fibers it is important to limit the TAA content in the final-product TPA to values on the order of maximally 0.01% by weight. The lowering of the TAA content occurring as a coprecipitate in the crude TPA, no matter whether the crude TPA has been obtained by the direct oxidation of p-xylene with atmospheric oxygen in a solvent or by the hydrolysis of crude DMT, can be accomplished either by physical means, e.g. by recrystallization, or by chemical means, e.g. by a suitable chemical conversion of the carbonyl function in the TAA. The removal of the TAA by physical as well as chemical methods is a very energy-consuming procedure due to the low solubility of TPA in water or other suitable solvents, and poses high demands on the resistance strength of the materials for the vessels wherein these operations are carried out.

A number of processes are known for effecting the recovery of terephthalic acid as a fiber-grade product from an aqueous solution. These processes usually involve one or more stages of crystallization to effect separation of the terephthalic acid from other materials contained in the terephthalic acid solution. For example, U.S. Pat. No. 3,452,088 discloses a process for effecting the recovery of crystalline terephthalic acid from an aqueous solution at a temperature of from 392°–700° F. and at a pressure to maintain the water in the liquid phase substantially saturated with the terephthalic acid solute. This solution contains from 400°–600° p.p.m. of p-toluic acid based on the terephthalic acid. Recovery is effected by crystallization with controlled rate evaporative cooling from a temperature in the range of from 392°–700° F. to a temperature in the range of about 250°–300° F. followed by recovering the terephthalic acid crystalline produce by solid-liquid separation at a temperature in the range of 250°–300° F. and at a pressure sufficient to maintain the water in the liquid phase.

Other processes involving the oxidation of a xylene and the subsequent recovery of terephthalic acid or a related acid from aqueous solutions by controlled crystallization are described in U.S. Pat. Nos. 3,683,018; 3,839,436; and 3,850,983.

The patent to Meyer (U.S. Pat. No. 3,584,039) discloses a procedure for producing fiber-grade terephthalic acid from an impure terephthalic acid having an aldehyde impurity and other color-causing impurities which involves treating an aqueous solution containing the impure terephthalic acid with hydrogen at an elevated temperature and at a pressure sufficient to maintain the solution in the liquid phase in the presence of a group VIII noble metal catalyst, followed by separating the treated solution from the catalyst, crystallizing the terephthalic acid from the separated solution, while retaining the impurities and the reduction products dissolved in the mother liquid, and thereafter separating the mother liquid as a liquid phase containing the dissolved impurities and reduction products from the crystals of fiber-grade terephthalic acid.

U.S. Pat. No. 4,053,506 describes a process for the production of fiber-grade terephthalic acid or isophthalic acid wherein the acid is recovered from a catalytic liquid phase oxidation effluent by crystal size classification and acetic acid mother liquid displacement with hot fresh acetic and followed by quenching a suspension of terephthalic acid crystals in a hot solvent with colder fresh acetic acid solvent and separation of the product crystals. This technique is said to eliminate the need for separately purifying crude terephthalic acid or isophthalic acid or of converting these acids to the respective dimethyl ester and purifying the ester.

Since, for certain applications of polyesters on the basis of polyethylene terephthalate and polytetramethylene terephthalate, the use of DMT is preferred; while in other applications of these polyesters, TPA serves best as the starting product, there is the need for making it possible, starting from a basic process, to manufacture fiber-grade DMT as well as fiber-grade TPA as polyester raw materials in any desired mutual proportion under equal expenses.

It has now been found that the content of terephthalaldehydic acid methyl ester can be lowered by an improved distillation procedure to such an extent that the content does not exceed 1,000 p.p.m., so that by means of a multi-stage hydrolysis, according to this invention, terephthalic acid can be isolated without repeated recrystallization, at a purity level required for being processed directly into polyester fibers and filaments. Thus, the process of the invention is advantageous from an energy viewpoint.

It is an object of the invention to produce directly from a crude DMT, a terephthalic acid, suitable for manufacturing polyester fibers, by means of hydrolysis, wherein no use is made of the step of recrystallization of the crude DMT from methanol customary in the Katzschmann process or of a corresponding step of recrystallization of the thus-obtained terephthalic acid. The method leading to the crude DMT utilized in the process of this invention corresponds, in part, to the process scheme disclosed in *Hydrocarbon Processing*, November 1977, page 147. This crude DMT is suitable for producing a TPA that lends itself to the manufacture of polyester fibers, by means of hydrolysis, wherein the TPA obtained in the hydrolysis stage is formed from a reaction medium controlled in such a way that recrystallization of the TPA can be avoided.

This invention contemplates an integrated multi-stage process which involves production of a crude ester mixture containing DMT, distillation of the crude ester to produce a crude DMT substantially free of interfering impurities such as TAE, hydrolysis of the crude DMT in at least two stages to produce TPA and recovery of a purified TPA as well as recovery of methanol.

More particularly, the process of this invention is characterized by the following stages:

Oxidation and Esterification

A crude ester mixture containing DMT is produced by oxidizing p-xylene of technical purity and preferably a mixture of p-xylene and methyl p-toluate with gases containing molecular oxygen in the presence of an oxidation catalyst which contains cobalt, preferably a mixture of cobalt and manganese, at temperatures of 140°–170° C. and under pressures of 4–8 bar; and by esterifying the oxidation mixture with methanol at temperatures of 250°–280° C. and under elevated pressure. This process is disclosed in British Specification No. 1,344,383. The resulting crude ester mixture which results from the esterification of the oxidation mixture is fed directly into the distillation section.

Distillation

The resultant crude ester mixture is separated by distillation to form a low-boiling fraction enriched in methyl p-toluate and a low-boiling fraction enriched with intermediate oxidation products and other by-products which are recycled to the oxidation stage, a residual fraction of high boiling products and a crude DMT having a limited content of intermediate oxidation products, especially aldehydic compounds, i.e. the TAE is reduced to less than 1,000 p.p.m.

Hydrolysis

The crude EMT is hydrolyzed with water in at least two stages at a weight ratio of crude EMT to water of between 3:1 and 0.1:1 and at temperatures of between 140°–350° C. and under a pressure required to maintain a liquid phase in each stage, thereby initially yielding a reaction mixture containing terephthalic acid solids, dissolved terephthalic acid, methanol, monomethyl terephthalate, and by-products stemming from the crude DMT.

The hydrolysis of the crude DMT according to this invention is characterized by a first cocurrent stage and by a second countercurrent stage. In the first cocurrent stage, higher reaction temperatures are normally utilized. In the second countercurrent stage, lower temperatures are normally used to effect hydrolysis of the DMT with demineralized water.

Generally, the residence in the first hydrolysis stage is less than in the second hydrolysis stage in that the first stage serves to effect a higher initial conversion of the DMT to TPA; whereas the second stage serves to promote further hydrolysis and purification of the initial hydrolysate.

In the first hydrolysis stage, the temperature is usually from 140° to 350° C. and preferably from 240° to 280° C., with the pressure being in a range of from 6 to 200 bar, preferably 35 to 80 bar.

In the second stage hydrolysis, the temperature is from 150° to 300° C., preferably 180° to 220° C., with pressures of from 6 to 100 bar, preferably 8 to 30 bars.

More particularly, the preparation of TPA includes the following steps:

(1) the reaction mixture formed in the first hydrolysis stage is separated at temperatures of between 150° and 300° C. and under a pressure required to maintain a liquid phase by crystallization of the TPA into a suspension containing the terephthalic acid solids and into a solids-free liquid phase containing the remaining components including methanol, with a portion of the liquid phase forming a mother liquor or carrier liquid for the suspension;

(2) the mother liquor of the suspension in step (1) is replaced with pure demineralized water in the second stage of hydrolysis and the displaced mother liquid is combined with the solids-free liquid phase of step (1);

(3) the pressure on the resultant suspension of pure water and terephthalic acid obtained from step (2) is reduced to normal pressure the pure terephthalic acid is obtained by means of a solid-liquid separating operation, washing with pure, fresh water introduced into the process, and the filtrate is recycled into step (2);

(4) the pressure on combined liquids of step (2) is reduced to such an extent that the dissolved terephthalic acid is precipitated while the by-products remain in solution, and the thus-precipitated terephthalic acid is separated from the liquid phase and recycled into the reaction mixture of step (1);

(5) the liquid phase remaining in step (4), which contains by-products, is divided, in order to separate the methanol, by distillation into a water-methanol mixture discharged overhead and into an aqueous phase obtained in the sump, having a sump temperature of between about 100° and 280° C.; this aqueous phase is further processed to eliminate the by-products and to obtain residual amounts of terephthalic acid; and the thus-formed mother liquor is recycled into the process.

Figure 5:
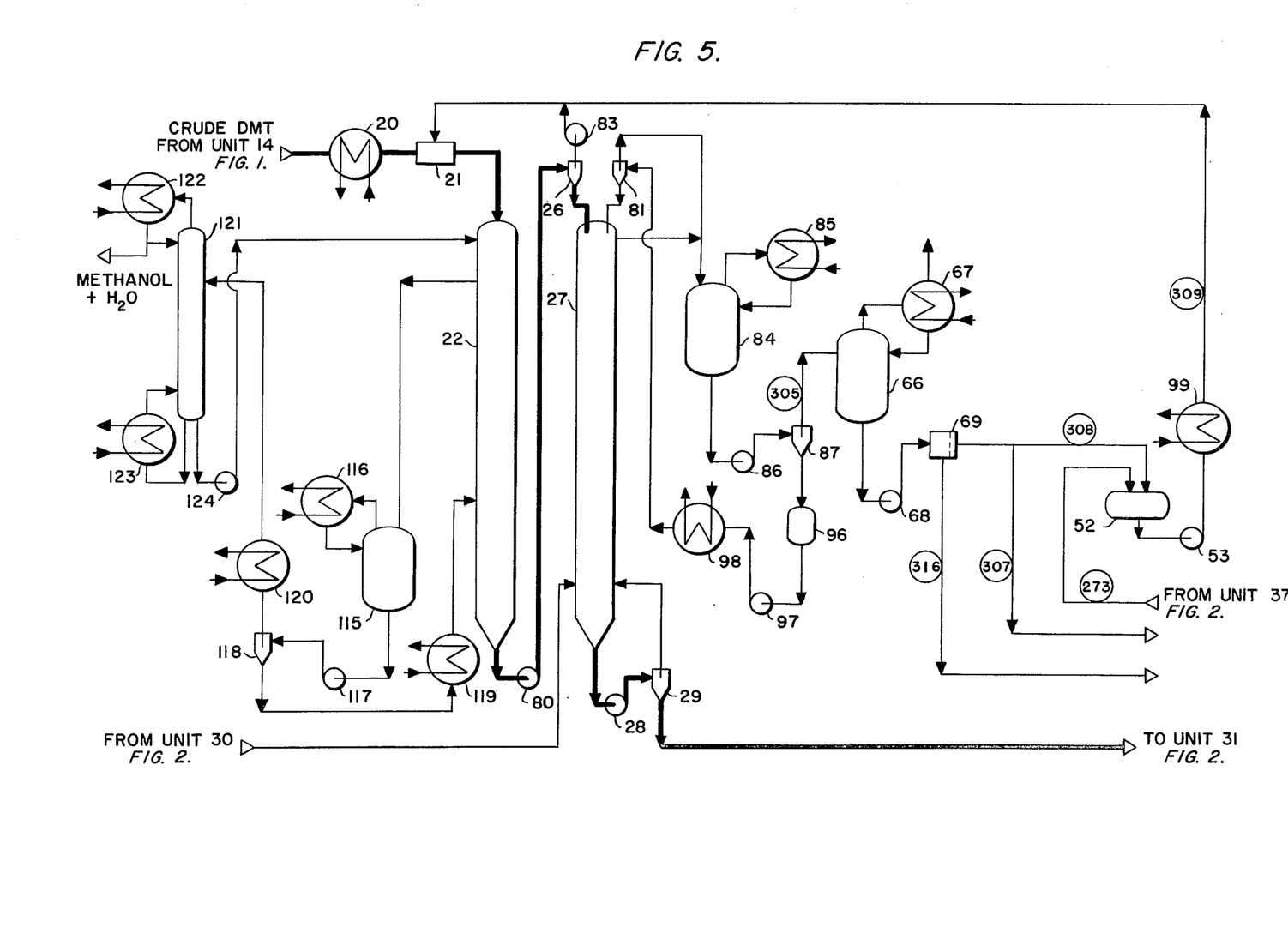
FIG. 5 is a schematic flow sheet illustrating an embodiment of the process wherein methanol is removed from the initially formed hydrolysate directly from the first stage hydrolysis reactor and an embodiment of a working-up system for effecting recovery of TPA and other products.

The weight ratio of the crude DMT used as a starting material and water determines the equilibrium position and thus the conversion during the hydrolysis reaction. It can be seen therefrom that the conversion rises with an increasing water proportion. The amount of excess water employed is limited for energy-preserving reasons. The optimum of the weight ratio of the crude DMT and water is, at temperatures of between 250° and 260° C., at values of about 0.2:1 to 0.4:1. The quantity of water utilized is selected so that the methanol concentration in the reaction mixture exiting from the first stage hydrolysis reactor ranges between 5% and 30% by weight, and the degree of conversion, based on TPA, is approximately 50–85%. With an appropriately selected residence time, an equilibrium is obtained which corresponds to the concentration of the reactants and the temperature. To further shift the equilibrium toward the side of the hydrolysis products, the methanol can be transferred out of the initial reaction mixture even before hydrolysis is completed in the first stage reactor (as shown in FIG. 5).

Below a temperature limit for the hydrolysis lying at about 220° C., the conversion rate of the hydrolysis is too low, based on the economical exploitation of a corresponding manufacturing plant required; at above 300° C., the pressures occurring and the energy consumption become so high that economical operation is no longer ensured. Accordingly, as heretofore indicated, the preferred temperature range in the first stage of hydrolysis is from 220° to 300° C. and most preferably from 240° to 280° C.

The proportion of water as related to the crude DMT is furthermore of importance due to the function of water as a solvent for the by-products forming during the hydrolysis. The axiom applies that the proportion of water must be higher, the higher the proportion of the by-products stemming from the crude DMT as related to the TPA, so that these by-products can be maintained in solution in correspondence with their solubility during the crystallization of the TPA produced.

Finally, the water also acts as a transport agent for the reactants of the process of the invention.

Figure 2:
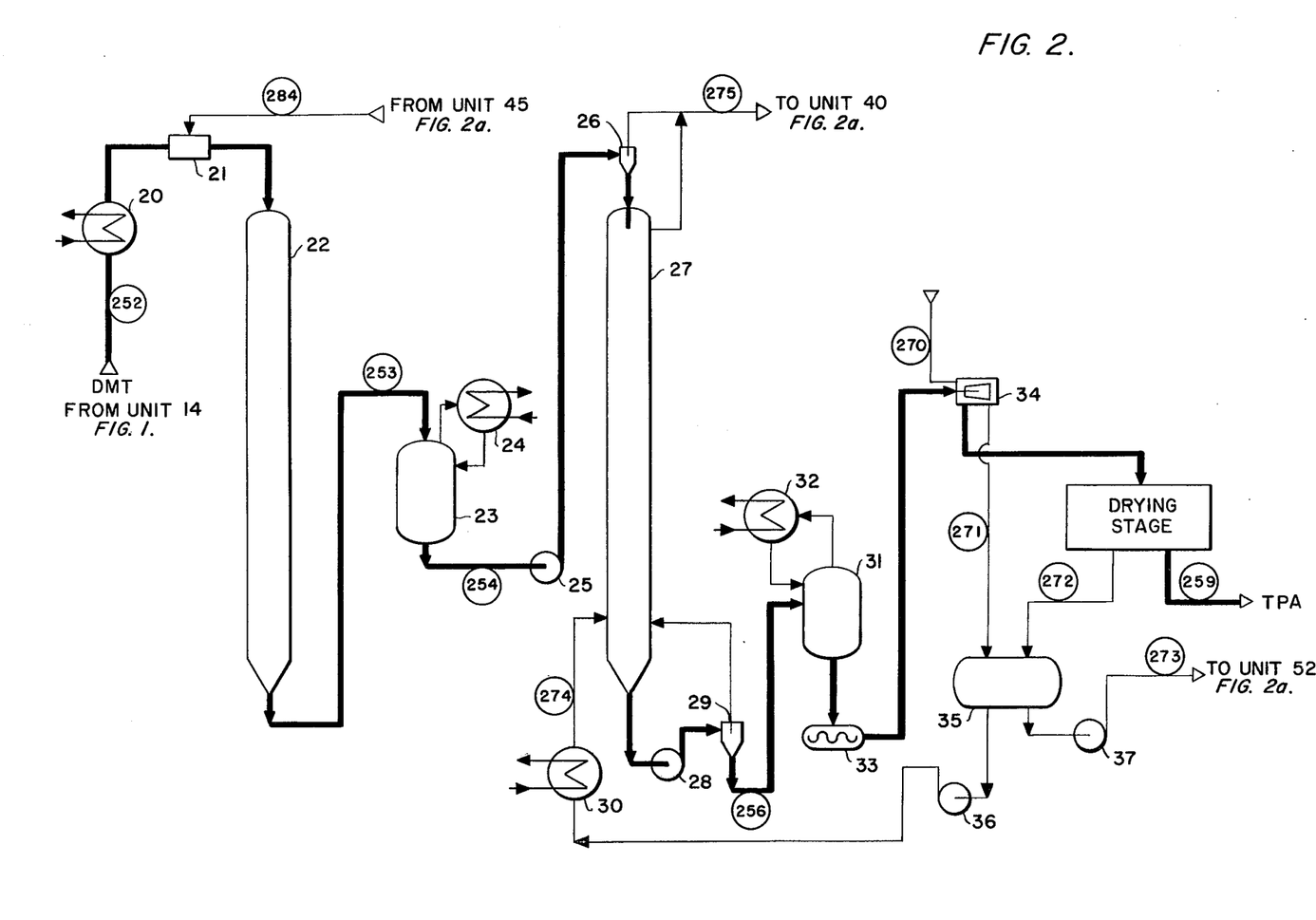
FIG. 2 is a schematic flow sheet illustrating one embodiment of an apparatus for effecting two-stage hydrolysis of the crude DMT having a reduced TAE content and the subsequent recovery of the crystallized TPA.

The hydrolysis is initially conducted by passing the reaction mixture through the first reactor from the top toward the bottom cocurrently with the water; during this step, there are formed from the crude DMT, with the progressing reaction, monomethyl terephthalate (MMT), TPA, and methanol, as well as the conversion products formed from the by-products of the crude DMT (see FIG. 2).

The reaction mixture discharged from the first reactor is, according to a preferred mode of operation, cooled to 200° C. and expanded to 20 bar, so that only pure TPA is precipitated. The resultant crystalline sludge is separated in a solid-liquid separating operation, for example in a hydrocyclone, into a suspension containing the TPA having a solids content of about 40%, and thus still being readily transportable in the process, and into a phase consisting essentially of mother liquor and methanol.

Further cooling would lead to the precipitation of impurities during hydrolysis. Therefore, mother liquor is replaced by demineralized water in the second hydrolysis stage. During the subsequent dilution, the last traces of monomethyl terephthalate (MMT) are reacted. The demineralized water used in the second hydrolysis stage comes directly from the water conditioning plant, since here the requirements regarding water purity are highest. In this hydrolysis stage, the terephthalic acid is present in high purity, whereas a recirculated process water, with traces of impurities, is used in the first hydrolysis stage. This procedure is of importance since all by-products and/or impurities are still present in the first hydrolysis stage.

The separation and recovery of the TPA after expansion and cooling to temperatures of between 220° and 180° C., however, can also be accomplished by means of a centrifuge while washing with demineralized water, the mother liquor being further processed.

The hydrolysis is conducted in at least two stages, for example in two series-connected reactors; in an especially preferred embodiment of the invention; the reaction mixture is conducted, in the second hydrolysis stage reactor, countercurrently to the pure water agent with simultaneous washing of the thus-precipitated TPA crystals moving under the influence of gravity, and with displacement of the mother liquor.

The liquid stream of washing water rising countercurrently to the thus-formed TPA crystals displaces the mother liquor introduced with the crystals at the head of the second reactor, so that there are present on the bottom of this reactor merely the washing water introduced at that location, TPA crystals, as well as the TPA contained in the liquid phase in correspondence with its solubility, and so that at the head of the reactor the mother liquor, diluted by the washing water, can be discharged. By the washing water flowing countercurrently under hydrolysis conditions, the mother liquor is constantly diluted during its way through the reactor. Because of the simultaneously conducted step of completely removing the methanol, no MMT can be detected any longer on the bottom of the second reactor, since under the pressure and temperature conditions employed there is a further shift of the hydrolysis equilibrium $$MMT + H_2O \rightleftharpoons TPA + CH_3OH$$

toward the right-hand side of the reaction equation, and the solubility of MMT is substantially higher than the solubility of TPA. Thus, further hydrolysis of mono- and dimethyl esters of terephthalic acid is promoted in this second stage hydrolysis reactor, also crystallization of the TPA newly formed is promoted.

By utilizing the countercurrent principle in the countercurrent reactor, comparatively small amounts of water are consumed for purifying the TPA crystals as well as TPA crystals newly formed therein.

Figure 2A:
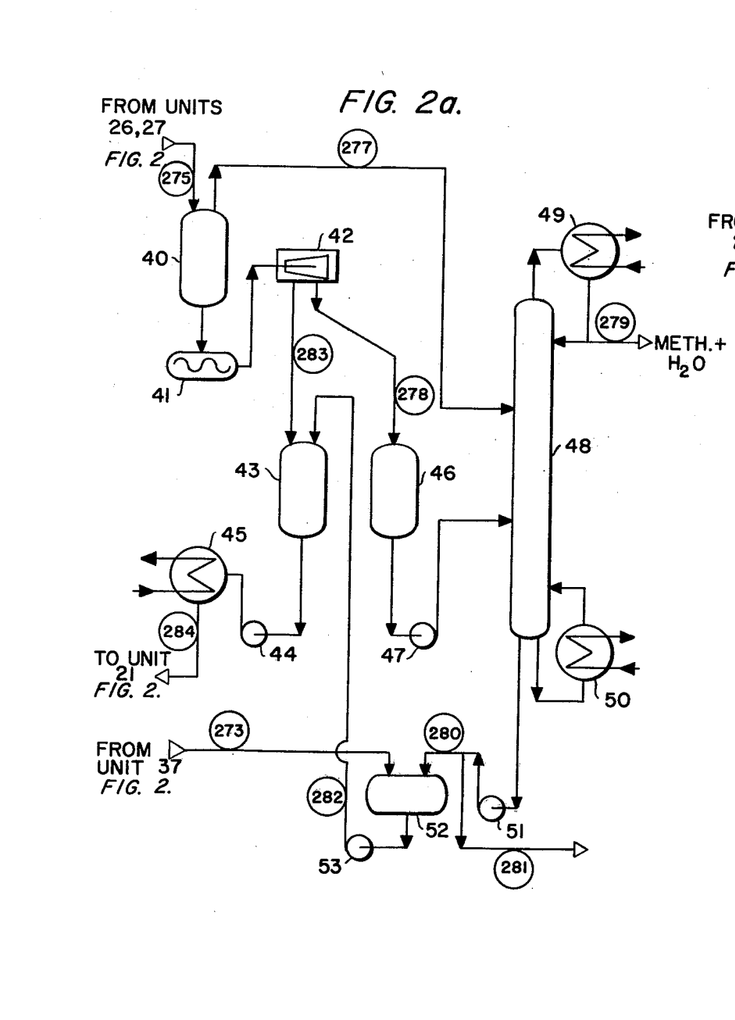
FIGS. 2a and 2b are schematic flow sheets which, respectively, show different embodiments of the process for working-up the liquid stream containing methanol and other by-products that are separated at the head of the second stage hydrolysis reactor.
Figure 2B:
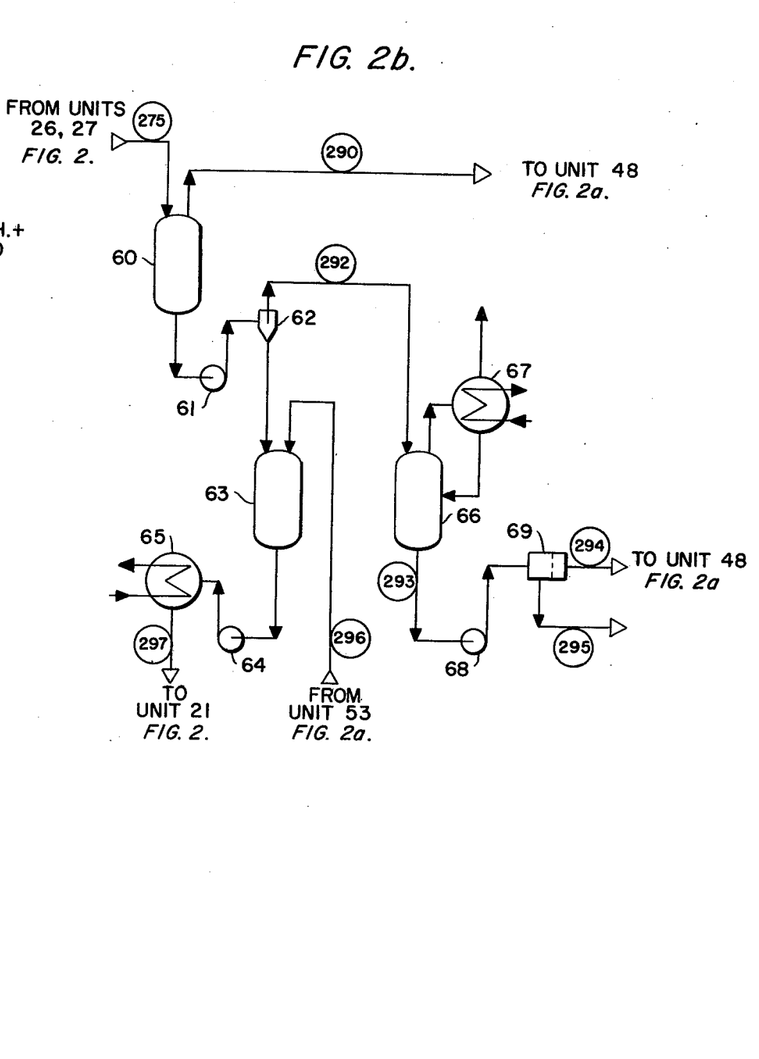
Figure 3:
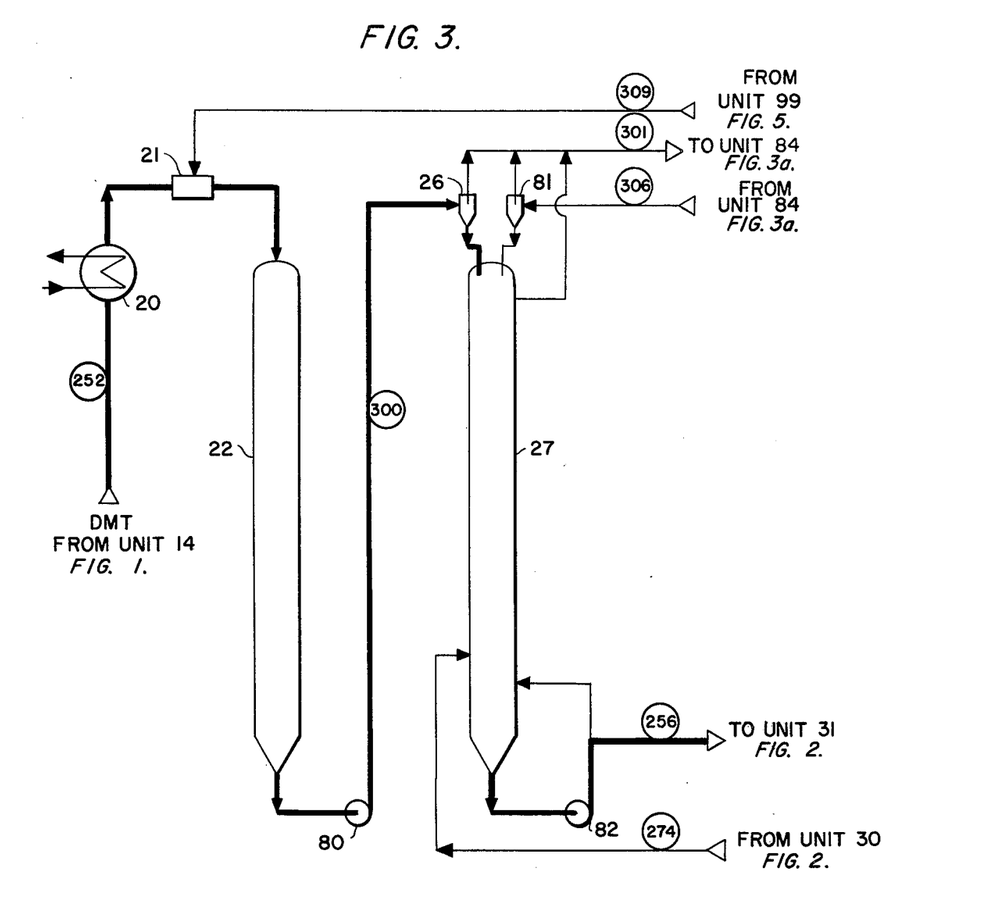
FIG. 3 shows yet another embodiment of a process for carrying out the two stage hydrolysis operation.
Figure 3A:
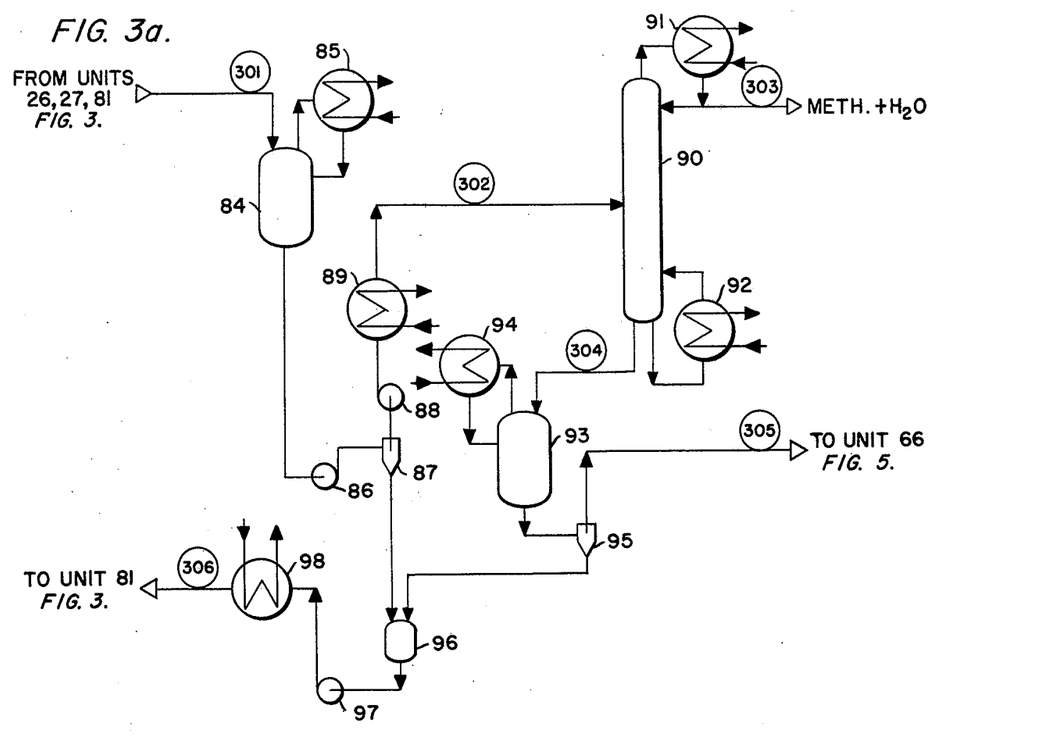
FIG. 3a is a schematic flow sheet of an apparatus and process for effecting the recovery of methanol and other by-products from the stream removed from the head of the second stage hydrolysis reactor.

All products present in the liquid phase are transported to the head of the second reactor (see FIGS. 2, 3 and 5) and/or of the third reactor (see FIG. 6), discharged therefrom, and partially recycled (FIG. 5) and fed to further processing in crystallizers (FIGS. 2a, 2b, 5 and 6) and/or subsequently to a post reactor (FIG. 3a).

Figure 4:
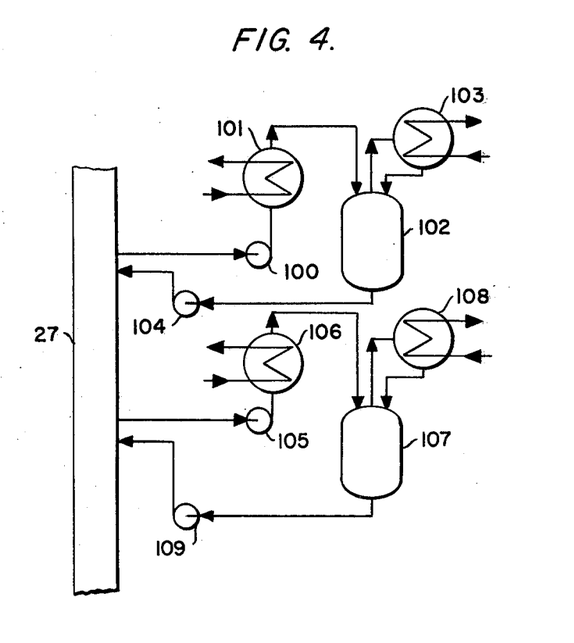
FIG. 4 is a schematic flow sheet of a process for effecting removal of by-products occluded on the crystals of TPA within the second stage hydrolysis reactor.

A portion of the suspension can be continuously withdrawn as a secondary stream from the countercurrent reactor, the solids proportion can be partially or completely dissolved by heating by 20°-100° C., expansion can then be effected, and the resultant suspension can be recycled into the countercurrent second reactor, as shown in FIG. 4. By means of this procedure, an even purer TPA is discharged at the bottom of the countercurrent reactor.

According to the process of this invention, a recrystallization of the TPA withdrawn at the second reactor bottom is unnecessary.

The withdrawn suspension of pure TPA in demineralized water is expanded by way of one or several stages and separated at normal pressure by means of a solid-liquid separating operation, for example, in a centrifuge while washing with demineralized water. It is impossible for impurities to be crystallized in the filtrate of the centrifuge.

The TPA discharged from the centrifuge is dried and stored. This TPA has a degree of purity of at least 99.99% by weight, corresponding to a content of by-products of maximally 100 p.p.m.

The liquid, withdrawn from the head of the countercurrent second reactor, can be combined with the mother liquor separated prior to entrance into the second reactor and can be expanded to normal pressure or to an intermediate pressure (FIGS. 2a and 2b). The thus-obtained solid matter is suitably separated from the mother liquor in a centrifuge or some other suitable apparatus. The mother liquor is fed to a methanol rectification stage. The methanol produced as the distillate can be reused for esterification during the production of the crude ester, while the aqueous phase obtained in the sump, wherein the by-products are dissolved, is either recycled or further worked up. Depending on the concentration of the by-products, part of the aqueous phase can be discharged to remove the by-products; the remaining portion can then be utilized for mixing with the solids separated by the centrifuge, and the thus-formed suspension can be recycled into the first hydrolysis reactor after heating to reaction temperature.

The mother liquor separated prior to entering the second reactor in the two-stage conductance of the hydrolysis can, however, also be recycled into the first hydrolysis stage (FIG. 5).

The washing liquid withdrawn at the head of the second reactor, as well as the mother liquor from the hydrocyclone can be present, in a preferred mode of operation, at 200° C. and 20 bar. The subsequent additional expansion and cooling steps are conducted so that dissolved TPA and MMT are precipitated while the other by-products, e.g. isomers, such as isophthalic acid (IPA) and orthophthalic acid (OPA) remain in solution.

The thus-produced solid matter is reheated with part of the mother liquor and recycled into the first reactor, whereas the mother liquor containing the remainder of the by-products is further expanded. The thus-crystallized products are separated in a suitable manner, for example on a filter or a centrifuge, and passed on to an isomer separating stage. The mother liquor is fed to the methanol rectifying stage as described above.

In the second hydrolysis reactor connected downstream of the first reactor, the suspension containing the thus-formed terephthalic acid crystals is conducted from above countercurrently to a water stream rising from the bottom toward the top. This second hydrolysis reactor is operated by the countercurrent method as described, for example, in U.S. Pat. No. 4,118,313. The water stream rising countercurrently to the thus-formed terephthalic acid crystals displaces the liquid phase introduced among the crystals as mother liquor at the head of the column, so that the only products remaining on the bottom of the second hydrolysis reactor are the water introduced at that point, terephthalic acid crystals, as well as the terephthalic acid contained in the mother liquor in accordance with its solubility. On account of the absence of methanol, the bottom of the second hydrolysis reactor no longer contains monomethyl terephthalate. All other by-products present in the liquid phase, i.e. the mother liquor of the suspension, are transported to the head of the second hydrolysis reactor and at this point are discharged from the reactor and passed on to further processing.

The intermediate product, crude DMT which is used as a starting material for the hydrolysis and which is obtained from a crude ester mixture, is brought by distillation to a content of maximally 0.1% by weight of TAE in accordance with a preferred embodiment of the invention. Thereby it is possible to operate in the hydrolysis stage with comparatively small amounts of water, which is especially advantageous from the viewpoint of conserving energy.

The process of this invention has the further advantage that there is no need for a catalyst in the hydrolysis process.

The process of this invention can be readily applied, for example, also to the analogous production of IPA from crude dimethyl ester of isophthalic acid (DMI), taking into account the somewhat different solubility relationships.

Suitable materials for the apparatus, containers, and conduits coming into contact with the reaction mixture under the reaction conditions during hydrolysis are types of steel which are mechanically strong and corrosion-proof under the reaction conditions due to the incorporation by alloying of steel-refining materials and due to special physical treatment procedures, and also nickel alloys, both so that in the final product TPA a total metal content of 10 p.p.m. is not exceeded. For the reactors used for the primary portion of the residence time of the reactants in the process under the pressure and temperature conditions used in the hydrolysis, it is also advantageous to employ titanium-plated steels.

The process of this invention in its mode of operation for preparing pure TPA will be described in greater detail below with reference to the accompanying drawing wherein.

Figure 1:
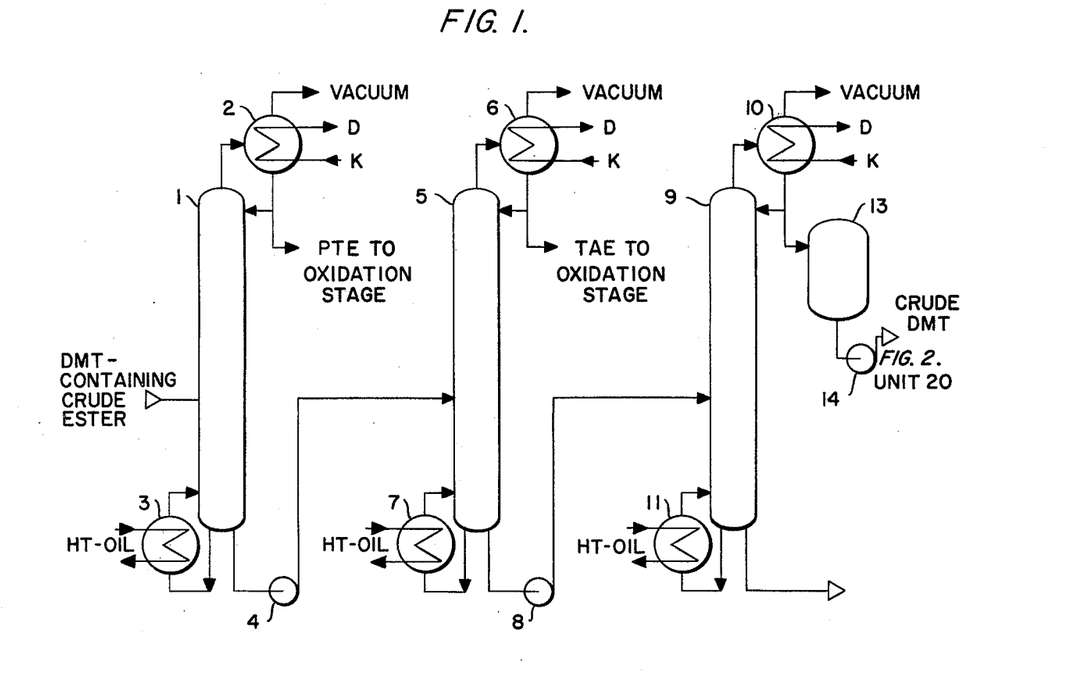
FIG. 1 is a schematic flow sheet illustrating one embodiment of an apparatus and process for effecting the separation of TAE from a crude ester mixture containing DMT and intermediate products occurring during the production of DMT.

FIG. 1 shows a mode of operation for producing a crude DMT with a TAE content of maximally 0.1% by weight. In column 1 equipped with condenser 2 and evaporator 3, a head fraction enriched in methyl p-toluate (PTE) under a reflux ratio of about 2:1 at a temperature of about 140° C. and a pressure of about 100 mbar is withdrawn from the crude ester coming from the esterification stage of a Witten process plant for producing BMT. The sump fraction at a temperature of about 200° C. is fed via pump 4 to column 5 with condenser 6 and evaporator 7; a TAE-enriched head fraction under a reflux ratio of about 3:1 to 10:1 at a temperature of about 130° to 190° C. and a pressure of about 15 to 100 mbar is withdrawn from column 5. The sump fraction of column 5 at a temperature of about 150° to 210° C. is fed via pump 8 to column 9 with evaporator 11, the head product of column 9 ist crude DMT: which is withdrawn under a reflux ratio of about 0.3:1 at a temperature of about 180° C. and a pressure of about 50 mbar and a high-boiling residue is the sump product at a temperature of about 240° C. The crude DMT containing no more than 0.1% TAE is collected via condensor 10 in container 13 and from there is conducted to heat exchanger 20 via pump 14.

Figure 1A:
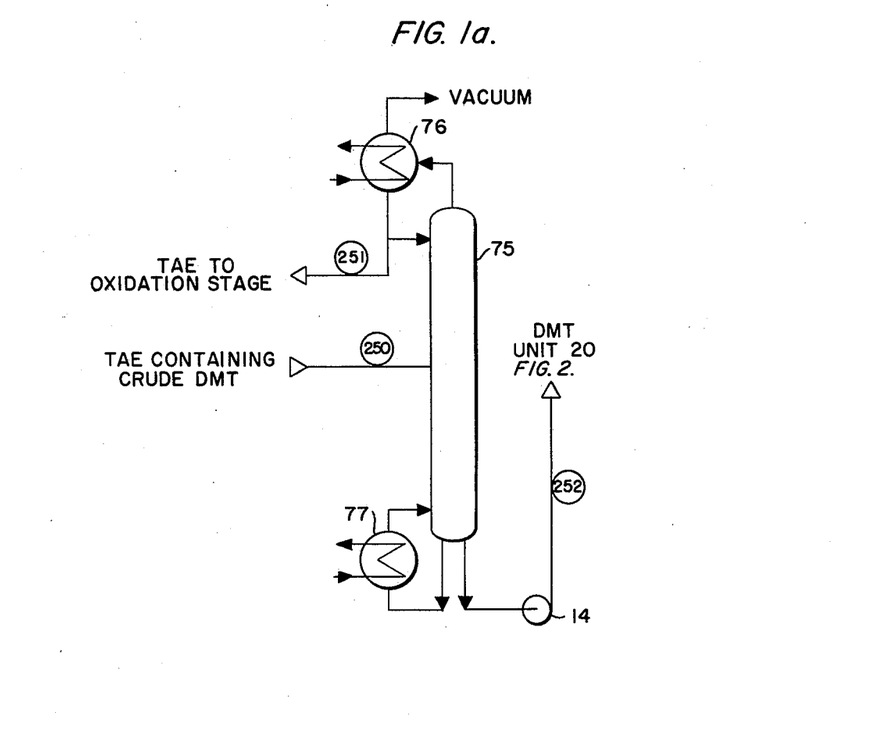
FIG. 1a is a schematic flow sheet of another embodiment of the distillation procedure for effecting removal of TAE from a crude DMT.

FIG. 1a shows a different mode of operation for producing the intermediate product, crude DMT which is the starting material utilized according to this invention; a TAE-containing crude DMT is reduced to a TAE content of maximally 0.1% TAE by withdrawing a TAE-enriched under a reflux ratio of about 3:1 to 10:1 at a temperature of about 130° to 190° C. fraction overhead. The sump temperature is about 150° to 210° C. The mode of operation shown in FIG. 1a is hereinafter described in greater detail in Examples 1 and 2.

According to FIG. 2, the crude DMT in the form of a melt is brought in heat exchanger 20 to the reaction temperature, preferably 220°–300° C., and fed to mixer 21 where it is mixed with an aqueous process stream returned from the process via heat exchanger 45 and likewise brought to reaction temperature. The aqueous process stream contains trace amounts of impurities, such as TAA, p-toluicacid, IPA, OPA, MMT. The mixture is fed to reactor 22. Here the hydrolysis takes place at a residence time which is dimensioned so that approximately the respective equilibrium condition is attained. Usually a period of about 40 minutes is appropriate to obtain a high degree of conversion, e.g. up to 85%. The reaction mixture is expanded in crystallizer 23 to such an extent that the largest portion of the TPA is crystallized. The vapors are condensed in condenser 24 and recycled into crystallizer 23. By means of pump 25, the suspension of TPA solids is fed tangentially to the hydrocyclone 26 and separated therein into a fraction rich in TPA solids suspended in a minor proportion of the liquid reaction mixture, which is introduced into the head of the reactor 27, and a fraction rich in mother liquor, which is conducted to the crystallizer 40. The solids proportion of the suspension, consisting of crystals of terephthalic acid, pass downwardly under the influence of gravity through the hydrolysis reactor 27 countercurrently to the fresh demineralized water introduced at the sump of the hydrolysis reactor 27 and the minor proportion of the liquid reaction mixture introduced with the suspension is admixed with the fresh water and is discharged from the top, i.e. head of the reactor 27, and is then combined with the separated reaction mixture liquid free of solids, i.e. the mother liquor.

The mother liquor withdrawn at the head of reactor 27 is combined with the fraction rich in mother liquor.

Additional hydrolysis occurs in reactor 27 under countercurrent conditions.

Demineralized water of the same temperature is fed via heat exchanger 30 at the sump of reactor 27, and the mother liquor in the suspension is exchanged countercurrently to the demineralized water. The thus-obtained suspension of pure TPA in demineralized water is discharged from the sump and conducted via pump 28 and hydrocyclone 29 to crystallizer 31 with condenser 32. This crystallization is conducted in several stages, depending on the circumstances. The head fraction of hydrocyclone 29 is recycled into the countercurrent reactor 27.

The crystal suspension exiting from crystallizer 31 is introduced by means of a metering pump 33 into centrifuge 34, where it is separated into TPA crystal solids, which are washed with demineralized water introduced at this point into the process and then conducted to the drying stage, and into washing water which is collected in the container for demineralized water 35. In container 35, the vapors from the TPA drying stage are also collected. From here the primary amount of the demineralized water is introduced, via heat exchanger 30 with pump 36, into countercurrent reactor 27; the remainder is fed to collecting tank 52 by means of pump 37. The dried, pure TPA is stored and from there passed on to the user.

In crystallizer 40 (FIG. 2a), the combined mother liquor from hydrocyclone 26 and the overflow from reactor 27 is expanded to normal pressure, optionally in several stages. During this operation, dissolved TPA, unreacted MMT as well as by-products are precipitated in solid form. The thus-obtained suspension is introduced by means of pump 41 into centrifuge 42 and separated from the liquid phase. The solid phase is mixed in container 43 with water from container 52 and recycled, by means of pump 44 via heat exchanger 45 into mixer 21 after having been heated to reaction temperature.

The liquid phase obtained at centrifuge 42 is fed via the collecting tank 46 with pump 47 to the methanol rectification tower 48 equipped with evaporator 50 and condenser 49. Furthermore, the vapors which are obtained during the expansion of the mother liquor in crystallizer 40 are conducted into the top portion of column 48. By means of condenser 49, a methanol-water mixture is removed from the process. The sump product of the rectifying tower 48 is withdrawn by means of pump 51. This sump product contains the by-products in an aqueous solution. Such an amount of solution is discharged from the process that the content in by-products in the cycle is maintained at a constant value. The remainder is conducted into the collector 52.

FIG. 2b shows another preferred embodiment of the working-up operation. This procedure is especially well suitable if higher contents of by-products are to be worked up. The mode of operation in reactor 22, crystallizer 23, reactor 27, as well as the crystallization and working up of the pure TPA withdrawn from reactor 27 takes place in the same way as in the description of FIG. 2.

In contrast, to the working-up operation depicted in FIG. 2a, there is no expansion to normal pressure in crystallizer 60; rather, as indicated in FIG. 2b, expansion is conducted to an intermediate pressure corresponding to such a temperature that the by-products remain in solution; whereas only the TPA and MMT are extensively separated by crystallization and conducted via pump 61, enriched in hydrocyclone 62, into the container 63. From there the TPA and MMT, as described above, are recycled via pump 64 and by way of heat exchanger 65 into mixer 21. The top stream of the hydrocyclone 62 is further expanded in crystallizer 66 with condenser 67. By means of pump 68 the resulting suspension is introduced on filter unit 69. The solid matter is further worked up in an isomer separating stage to remove the by-products. The filtrate is introduced into the methanol rectification tower 48, as shown in FIG. 2a.

Another preferred mode of operation of this process is illustrated in FIGS. 3 and 3a of the drawings. This procedure differs from the mode of operation described with reference to FIG. 2 essentially in that the hydrolysis is conducted in reactors 22 and 27 under identical pressure and at identical temperature. The top streams from cyclones 26 and 81, as well as the top stream from reactor 27, are combined and expanded to such an extent that only TPA is precipitated and is then separated and recycled into reactor 27. The mother liquor, which contains in addition to water also methanol, MMT, and by-products, is fed into a reactor 90. The reactor is operated under such a pressure that, by distilling off a methanol-water mixture, the equilibrium in the lower portion of the reactor is shifted toward the side of TPA.

The thus-produced TPA remains in solution at the pressure and temperature conditions employed. After leaving the reactor 90, TPA is crystallized from this solution by cooling and expansion, and this TPA is recycled into reactor 27; whereas the by-products are discharged, as will be explained below.

The crude DMT is brought, in the form of a melt, to the reaction temperature in heat exchanger 20 and mixed, in mixer 21, with an aqueous stream recycled from the process, which likewise has been brought to the reaction temperature; this mixture is fed to reactor 22. The entire reaction mixture is introduced, via a pump 80, tangentially into hydrocyclone 26 and separated into a liquid phase and a suspension. The suspensions from hydrocyclones 26 and 81 are introduced to the head of reactor 27. The solid proportion of the suspension, consisting of terephthalic acid, runs under the force of gravity through reactor 27 countercurrently to demineralized water fed at the sump of the reactor.

The reaction mixture is discharged from the sump of reactor 27 and fed by means of pump 82 to crystallizer 31, which is operated in accordance with the crystallizer 23 shown in FIG. 2.

The liquid phase forming the rising stream in reactor 27 is withdrawn overhead. This liquid phase is a mixture saturated with dissolved TPA and contains methanol, MMT, and the by-products stemming from the crude DMT. Together with the head fractions from hydrocyclones 26 and 81, the ascending liquid phase constitutes the process stream from which the by-products are withdrawn.

The liquid stream withdrawn from the head of reactor 27 is expanded in crystallizer 84 with condenser 85 and cooled during this operation (FIG. 3a). The expansion vapors condensed in condenser 85 are recycled into crystallizer 84. The thus-obtained crystalline sludge is fed by way of pump 86 to hydrocyclone 87, the bottom fraction of which is recycled into the process via hydrocyclone 81 as a suspension via storage tank 96, pump 97, and heat exchanger 98. During the heating step with the aid of heat exchanger 98, part of the solids of the suspension is redissolved.

The top fraction from hydrocyclone 87 contains, in addition to the by-products stemming from the crude DMT, substantially unreacted MMT, as well as methanol. This fraction is introduced via pump 88 and heat exchanger 89 to reactor 90 which serves as a distillation column for separation of methanol and $H_2O$ and also as a secondary reactor for the unreacted mono-methyl terephthalate. For this purpose, the distillation of the liquid phase containing the by-products within column-reactor 90 is conducted at a temperature at which the terephthalic acid produced by the secondary hydrolysis of monomethyl terephthalate with the aqueous phase accumulating in the sump of the column remains dissolved in the aqueous phase. Since, under the conditions of the distillation, the methanol from the aqueous phase is constantly removed, the reaction of monomethyl terephthalate to terephthalic acid in the aqueous phase takes place very quickly. In the enrichment section of the column, the residual impurities are accumulated in addition to water and terephthalic acid dissolved therein, at sump temperatures of between about 200° and 280° C. In heat exchanger 92, the energy is supplied which is necessary for the evaporation of methanol and $H_2O$. The vapors obtained at the head are condensed in condenser 91, and the thus-obtained water-methanol mixture is withdrawn.

The sump product from the column-reactor 90 is continuously withdrawn and cooled by expansion to such an extent that the terephthalic acid is crystallized and can be recycled, after separation, into the hydrolysis stage; whereas the by-products remain in solution. By additional cooling or evaporation of a filtrate obtained during the solid-liquid separation of the TPA, the by-products are separated, and the aqueous filtrate, after passing a water processing stage, is again recycled into the first hydrolysis reactor of the hydrolysis stage.

The sump product of reactor 90 is expanded in crystallizer 93 and cooled during this step. The thus-produced expansion vapors are recycled into the crystallizer.

The crystalline sludge is thickened in hydrocyclone 95 and recycled into the process.

The overflow from hydrocyclone 95 is introduced into crystallizer 66 and expanded to remove by-products (FIG. 2b). Depending on the content of by-products, here again an analogous mode of operation acording to FIG. 2a can be conducted. The proposed procedure of separating the methanol under pressure can also be effected if the partial cooling described in connection with FIG. 2 is conducted between reactor 22 and reactor 27.

FIG. 4 shows an embodiment making it possible in an especially advantageous manner to dissolve the produced TPA crystals by slight heating in the mother liquor and then to recrystallize a product of greater purity again by expansion. Thereby, any occluded by-products are dissolved and are passed on for purposes of post reaction or removal to the head of reactor 27. This mode of operation is preferably employed if the crude DMT shows a higher content of by-products. By means of pump 100, crystalline suspension is removed from reactor 27, brought to an elevated pressure, and heated in heat exchanger 101. The crystalline sludge is dissolved entirely or partially; the solution is expanded in crystallizer 102 and then the vapors are condensed in condenser 103 and recycled and the thus-produced suspension is recycled via pump 104 into reactor 27. This circulation can be provided repeatedly, as illustrated (note the arrangements of units 105–109).

FIG. 5 shows an embodiment of the process of this invention wherein the discharge of the methanol takes place directly from reactor 22. For this purpose, a large portion of the liquid phase of the reaction mixture is expanded in crystallizer 115 equipped with condenser 116, cooled, and the TPA is crystallized out. The thus-obtained suspension of TPA solids is fed via pump 117 to hydrocyclone 118, the bottom fraction of which is introduced as a suspension via heat exchanger 119 back into the reactor 22. While the suspension is heated by means of heat exchanger 119, a portion of the TPA solids of the suspension is redissolved.

The top fraction of hydrocyclone 118 is recycled via heat exchanger 120 to the methanol distillation column 121 equipped with condenser 122 and heat exchanger 123. The methanol distillation is operated as described in connection with FIG. 3a for the reactor or column 90. The sump product of the methanol column 121, however, is not crystallized but rather recycled via pump 124 into reactor 22. Furthermore, FIG. 5 shows a variation wherein, to optimize the amount of water employed, a part of the liquid phase of the reaction mixture from reactor 22 is reintroduced as the top fraction from hydrocyclone 26 via pump 83 into mixer 21.

FIG. 5 shows furthermore the working-up section with crystallizer 84 for the top fraction of hydrocyclone 81 and the top fraction withdrawn from the head of reactor 27. The suspension withdrawn from crystallizer 84 is separated by way of pump 86 in hydrocyclone 87 into a top fraction fed to crystallizer 66 and a bottom fraction recycled via collector 96, pump 97, and heater 98 and hydrocyclone 81 into reactor 27. From crystallizer 66 equipped with condenser 67, the suspension is introduced by means of pump 68 into filter 69. The thus-separated solid matter is further worked up, whereas the filtrate if fed via collecting tank 52, pump 53 and heater 99 into the mixer 21.

Figure 6:
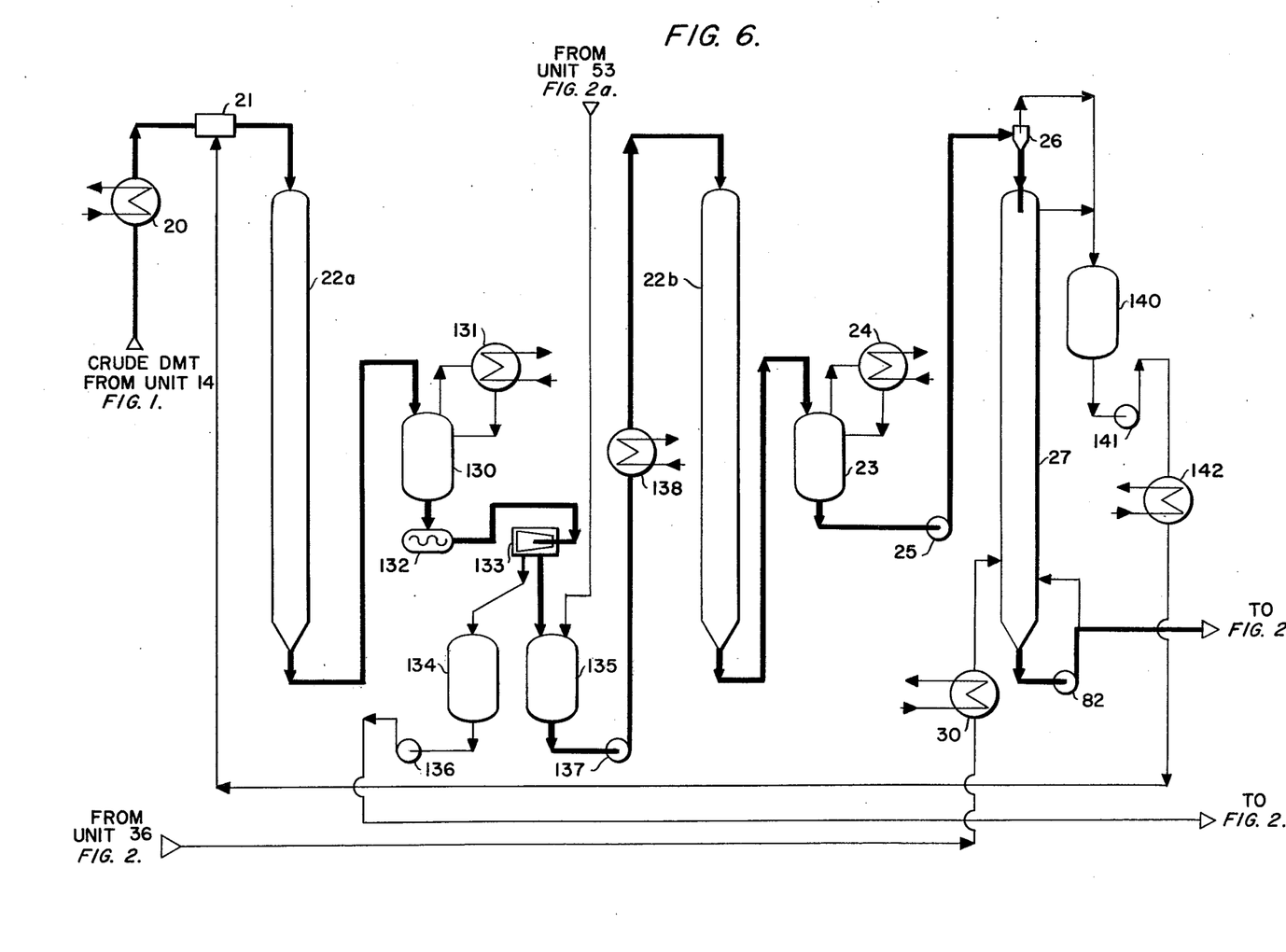
FIG. 6 is a schematic flow sheet that illustrates a multi-stage arrangement for effecting the hydrolysis of the crude DMT in three stages.

FIG. 6 shows a multi-stage arrangement for the hydrolysis in reactors 22a, 22b, and 27 with, respectively, series-connected crystallization stages to remove the by-products of the process of this invention contained in the liquid phase. In this arrangement, especially lower weight proportions of crude DMT to water can be utilized, for example 0.5:1.

The mode of operation of this invention will be described in even greater detail with reference to the following Examples 1 and 2.

The percentages in the examples refer to weight percent. The reference numerals refer to those figures in the various drawings.

EXAMPLE 1

Distillation is conducted in an apparatus as shown in FIG. 1a, with 23,582 kg./h. of crude DMT containing 96.13% DMT, 1.2% MMT, 0.1% PTE, 0.7% p-toluic acid (PTA), 0.7% TAE, 0.36% dimethyl orthophthalate (DMO), 0.46% DMI, and 0.35% of high-boiling compounds (HB), adjusting a reflux ratio of 8:1; thus obtaining 1,179 kg./h. of head product and 22,403 kg./h. of sump product. The temperature of the sump is maintained at 197° C. by evaporator or reboiler 77 and the temperature of the condenser 76 is held at 180° C. at a pressure of 55 mbar.

The head product contains 68.2% DMT, 13.1% TAE, the remainder being other by-products.

The sump product is composed of 0.05% PTE, 0.4% PTA, 0.05% TAE, 0.2% DMO, 0.4% DMI, 97.6% DMT, 1.0% MMT, and 0.3% high-boiling compounds (HB) and is subjected, together with 114,278 kg./h. of product from the recycled stream 284, to a hydrolysis at 250° C. and under 50 bar with a residence time of 40 minutes in the first stage hydrolysis reactor 22 as shown in FIG. 2.

Stream 284 has the following composition: 89.67% $H_2O$, 0.05% MeOH, 2.35% terephthalic acid (TPA), 0.15% isophthalic acid (IPA), 0.07% orthophthalic acid (OPA), 0.92% DMT, 0.01% DMI, <0.01% DMO, 6.24% MMT, 0.05% monomethyl isophthalate (MMI), 0.03% monomethyl orthophthalate (MMO), 0.23% PTA, 0.06% TAA, and 0.18% HB.

The reaction mixture discharged as the stream 253 from hydrolysis reactor 22 has, with a total quantity of 136,681 kg./h., the following composition:

71.98% $H_2O$, 5.35% $Ch_3OH$, 11.45% TPA is dissolved form, 4.25% TPA in solid form, 0.17% IPA, 0.08% OPA, 0.82% DMT, 0.01% DMI, <0.01% DMO, 5.29% MMT, 0.06% MMI, 0.03% MMO, 0.26% PTA, 0.07% TAA, and 0.20% HB.

By expansion to 200° C. and 20 bar in crystallizer 23, the stream 254 containing a suspension of TPA solids in an aqueous mother liquor is obtained. The composition is as follows:

71.98% $H_2O$, 5.35% $CH_3OH$, 1.93% TPA in dissolved form, 13.76% TPA in solid form, 0.17% IPA, 0.08% OPA, 0.82% DMT, 0.01% DMI, <0.01% DMO, 5.29% MMT, 0.06% MMI, 0.03% MMO, 0.26% PTA, 0.07% TAA, and 0.20% HB.

Via pump 25, stream 254 is fed in an amount of 136,681 kg./h. to hydrocyclone 26, the top fraction of which is combined with the liquid withdrawn from the head of hydrolysis reactor 27 to obtain stream 275. Stream 275 has a total quantity of 119,804 kg./h. under a pressure of 20 bar and at a temperature of 200° C. The composition of stream 275 is as follows:

83.69% $H_2O$, 6.10% $CH_3OH$, 2.25% TPA, 0.19% IPA, 0.09% OPA, 0.94% DMT, 0.1% DMI, 0.05% DMO, 6.04% MMT, 0.06% MMI, 0.03% MMO, 0.30% PTA, 0.07% TAA, and 0.22% HB.

Stream 275 is fed to further processing, described hereinbelow, to remove the methanol, the by-products, and still usable products, such as MMT.

The bottom fraction from hydrocyclone 26 is fed to hydrolysis reactor 27. At the bottom of reactor 27 a suspension is withdrawn at 200° C. and 20 bar via pump 28 and hydrocyclone 29 as product stream 256 with a total quantity of 46,888 kg./h. and with the following composition:

59.98% $H_2O$, 1.08% TPA in dissolved form and 38.94% TPA in the solid phase.

At the same time, the head fraction of the hydrocyclone 29 is returned into the lower portion of reactor 27.

By expansion to normal pressure, i.e. atmospheric pressure, and cooling to 100° C., the dissolved TPA is crystallized and, in centrifuge 34, separated, washed and thereafter dried. As the washing liquid, stream 270, provides 29,384 kg./h. of demineralized water (electric conductance $0.9.10^{-6}$ Siemens $[\Omega^{-1}]$ at 20° C.) under normal pressure and at 80° C. By the water added as the washing liquid, the amount of water required for the reaction is introduced into the process, and the water losses are also replaced in this manner.

As stream 259, 18,750 kg./h. of TPA is obtained of 99,99% purity, i.e. fiber-grade quality. The color number of 5% terephthalic acid solution in dimethylformamide is between 5 and 10 APHA.

As the stream 271, 55,389 kg./h. of washing water is obtained, containing 99.97% $H_2O$ and having a temperature of 95° C.

30.011 kg./h. from streams 271 and 272 is recycled as stream 274 via heat exchanger 30 into reactor 27 at 200° C. and 20 bar. 27,511 kg./h. is withdrawn as stream 273 from container 35 and fed to intermediate tank 52.

Stream 275 is expanded in crystallizer 40 to normal pressure and cooled to 100° C. during this step, thus crystallizing TPA and MMT. The thus-obtained vapors, stream 277 with a total amount of 23,050 kg./h. and a composition of 85.7% $H_2O$, 14.3% $CH_3OH$, and traces of solids is passed into the methanol column 48. The crystalline sludge is separated in centrifuge 42. The solid fraction, stream 283, in an amount of 11,451 kg./h., has the following composition:

9.31% $H_2O$, 0.47% $CH_3OH$, 22.94% TPA, 0.03% IPA, 0.01% OPA, 7.27% DMT, <0.01% DMI, <0.01% DMO, 59.86% MMT, 0.01% MMI, <0.01% MMO, 0.04% PTA, 0.01% TAA, and 0.03% HB.

The filtrate, stream 278, has, with a total quantity of 85,303 kg./h., the following composition:

93.13% $H_2O$, 4.65% $CH_3OH$, 0.07TPA, 0.26% IPA, 0.13% OPA, 0.34% DMT, 0.01% DMI, 0.01% DMO, 0.44% MMT, 0.09% MMI, 0.04% MMO, 0.41% PTA, 0.1% TAA, and 0.31% HB.

Via the receiver vessel 46, stream 278 is fed to the methanol column 48. As stream 279, 7,295 kg./h. of a methanol-water mixture with 99.5% methanol and 0.5% $H_2O$ is withdrawn overhead at 65° C. and 1 bar. As the sump product, 75,316 kg./h. is obtained at 105° C. and 1 bar with the following composition:

98.12% $H_2O$, 0.06% TPA, 0.21% IPA, 0.10% OPA, 0.29% DMT, 0.01% DMI, 0.01% DMO, 0.38% MMT, 0.07% MMI, 0.04% MMO, 0.35% PTA, 0.09% TAA, and 0.26HB.

Of this amount, 25,742 kg./h. is withdrawn as stream 281 to remove the by-products.

The remaining portion, stream 280, is conducted together with stream 273 via intermediate container 52 and pump 53 as stream 282 into the receiver vessel 43. Together with stream 283, the product is recycled as stream 284 via heat exchanger 45 into reactor 22.

EXAMPLE 2

In this run, 22,384 kg./h. of crude DMT obtained as the sump product in the TAE distillation column 75, FIG. 1a, composed of 97% DMT, 0.05% TAE, remainder: other by-products (stream 252), is subjected continuously to hydrolysis, together with 67,152 kg./h. of water from heat exchanger 99, stream 309, FIG. 5, in reactor 22, FIG. 3, at 250° C. and 50 bar with a residence time of 40 minutes. The reaction mixture withdrawn from hydrolysis reactor 22 as the stream 300 has a total quantity of 89,536 kg./h. with the following composition:

71.21% $H_2O$, 6.73% $CH_3OH$, 11.54% TPA in dissolved form, 2.8% TPA in solid form, 0.88% DMT, 6.52% MMT, 0.11% PTA, 0.09% IPA, 0.04% OPA, 0.01% TAA, and 0.06% HB.

(For the sake of clarity, in this breakdown and also in the following, the monoesters MMO and MMI, as well as unreacted DMO and DMI are not listed separately.)

Product stream 300 is tangentially fed to hydrocyclone 26, the head fraction of this hydrocyclone being combined with the head fraction from hydrocyclone 81 as well as the filtrate withdrawn from the head of countercurrent reactor 27, to form stream 301.

Stream 301 has a total quantity of 128,406 kg./h. at a pressure of 50 bar and a temperature of 250° C. with the following composition:

75.48% $H_2O$, 5.8% $CH_3OH$, 12.03% TPA in dissolved form, 0.76% DMT, 5.62 MMT, 0.11% PTA, 0.08% IPA, 0.04% OPA, 0.01% TAA, and 0.06% HB.

The bottom fraction of hydrocyclone 26 is fed to hydrolysis reactor 27. The residence time, based on the amount of pure TPA, in reactor 27 is 2.5 hours. At the bottom of reactor 27, a suspension is withdrawn by means of pump 82. Stream 256, a portion of which is recycled to the bottom of reactor 27, contains, at 250° C. and 50 bar, with a total quantity of 46,875 kg./h., the following:

55.98% H$_2$O, 32.83% TPA in the solid phase, and 7.2% TPA in dissolved form.

By expansion to normal pressure and cooling to 100° C., the dissolved TPA is crystallized and separated from the filtrate as in FIG. 2, whereafter it is washed and dried. The washing fluid, stream 270, is 11,648 kg./h. of demineralized water (electric conductance $0.9 \times 10^{-6}$ Siemens $[\Omega^{-1}]$ at 20° C.) is utilized under normal pressure and at 80° C. By the water added as the washing liquid, the amount of water required for the reaction is provided and the water losses occurring in the process are replenished.

As stream 259, 18,750 kg./h. of a terephthalic acid of 99.99% purity, i.e. fiber-grade quality, is obtained. The color number of a 5% terephthalic acid solution in dimethylformamide is between 5 and 10 APHA.

As stream 271, 37,690 kg./h. of filtrate is obtained having a 99.97% water content and a temperature of 90° C. 32.846 kg./h. from streams 271 and 272 is recycled as stream 274 via heat exchangers 30 into reactor 27 at 250° C. and 50 bar. 6,927 kg./h. is branched off and introduced as stream 273 to the intermediate tank 52, FIG. 5.

Stream 301 is expanded and cooled in crystallizer 84, FIG. 3a, with a temperature of 250° C. and a pressure of 50 bar, thus crystallizing TPA. The crystalline sludge is tangentially introduced into hydrocyclone 87. The head fraction from hydrocyclone 87 has, after passing the heat exchanger 89, in the form of product stream 302, a temperature of 250° C. and a pressure of 50 bar and, with an amount of 92,139 kg./h., has the following composition:

85.09% H$_2$O, 6.54% CH$_3$OH, 0.86% DMT, 6.34% MMT, 0.83% TPA in dissolved form, 0.12% PTA, 0.1% IPA, 0.05% OPA, 0.01% TAA, and 0.07% HB.

Stream 302 is fed to column 90. At the head of this column, as stream 303, 8,138 kg./h. of a methanol-water mixture with a methanol content of 90% is withdrawn at 212° C. and under a pressure of 50 bar.

From the sump of column-reactor 90, at a temperature of 257° C. and a pressure of 50 bar, 84,002 kg./h. of stream 304 is withdrawn, having the following composition:

91.5% H$_2$O, 8.12% TPA in dissolved form, 0.14% PTA, 0.1% IPA, 0.05% OPA, 0.01% TAA, and 0.08% HB.

Stream 304 is cooled by expansion in crystallizer 93. The crystalline sludge is fed tangentially to hydrocyclone 95, the bottom fraction of which is combined with the bottom fraction from hydrocyclone 87 and recycled into the process as stream 306 via hydrocyclone 81, FIG. 3.

Stream 306, after passing heat exchanger 98, has a temperature of 250° C. and a pressure of 50 bar and, with a total amount of 52,899 kg./h., has a composition of 53.75% H$_2$O, 2.69% CH$_3$OH, 40.0% TPA in solid form, 2.61% MMT, 0.35% DMT, 0.38% TPA in dissolved form, 0.08% PTA, 0.06% IPA, 0.03% OPA, 0.01% TAA, and 0.04% HB.

The bottom fraction from hydrocyclone 81 is recycled into hydrolysis reactor 27.

The head fraction of hydrocyclone 95 is obtained as stream 305 with a total amount of 67,370 kg./h. and is under a pressure of 5 bar and at a temperature of 150° C. Stream 305 contains 99.37% H$_2$O, 0.15% PTA, 0.22% TPA in dissolved form, 0.11% IPA, 0.06% OPA, 0.01% TAA, and 0.08% HB.

By further expansion in crystallizer 66, shown in FIG. 5, almost all of the dissolved components are precipitated, and these components are discharged onto filters 69 and fed as stream 316 in a quantity of 428 kg./h. to a so-called isomer separating stage.

From the filtrate, 6.715 kg./h. of waste water is discharged as stream 307 with a minor content of by-products, to avoid enrichment in corrosion products and similar substances. The residual portion of the filtrate is introduced as stream 308, together with stream 273, by means of pump 37, FIG. 2, into container 52 and reintroduced by means of pump 53 as stream 309 into the process by way of mixer 21, FIG. 3. Stream 309 consists of more than 99.5% water and small amounts of still dissolved products and, as mentioned above, represents a quantity of 67,152 kg./h.

What is claimed is:

1. A process for the preparation of fiber-grade terephthalic acid from an intermediate stage crude dimethyl terephthalate obtained from a crude ester mixture produced by the oxidation of p-xylene and/or methyl p-toluate with oxygen-containing gases in the presence of a heavy-metal-containing oxidation catalyst at an elevated temperature and under an elevated pressure; and by the esterification of the oxidation mixture with methanol at elevated temperature and elevated pressure, which comprises separating the resulting crude ester mixture by distillation into a methyl p-toluate-enriched fraction, a residual high boiling fraction, and a crude dimethyl terephthalate having a limited content of intermediate oxidation products including terephthalaldehydic-acid methyl ester and other by-products, the content of terephthalaldehydic acid methyl ester being limited up to 0.1% by weight based on the weight of the crude dimethyl terephthalate; subsequently hydrolyzing the crude dimethyl terephthalate with water at a weight ratio of the crude dimethyl terephthalate to water of between 3:1 and 0.1:1, and at temperatures of between 140° C. and 350° C. and under the pressure required to maintain the liquid phase to produce a reaction mixture containing crystalline fiber-grade terephthalic acid and then recovering the terephthalic acid from the reaction mixture; said hydrolysis of the crude dimethyl terephthalate being conducted in at least two stages, wherein in the first hydrolysis stage, a mixture of the crude dimethyl terephthalate and water is passed cocurrently through a first reactor column and a portion of terephthalic acid formed by hydrolysis is crystallized from the reaction mixture at temperatures of between 300° and 150° C., a suspension of terephthalic acid crystals in a mother liquid is separated from the reaction mixture and introduced into the second hydrolysis stage and the remaining portion of the reaction mixture containing methanol and water is discharged from the first hydrolysis stage; and in the second hydrolysis stage demineralized water is passed countercurrently to the suspension of terephthalic acid crystals in the mother liquor in a second reactor column, whereby the mother liquor is constantly diluted, replaced by the demineralized water, the motor liquor is withdrawn from the top of the second reactor column, and additional terephthalic acid is formed and crystallized within the length of the second reactor column during the continual hydrolysis.

2. A process according to claim 1, wherein a suspension of terephthalic acid crystals in demineralized water is withdrawn from the bottom of the second hydrolysis stage and fiber-grade terephthalic acid is recovered therefrom.

3. A process according to claim 1, wherein the mother liquor is further cooled whereby still dissolved terephthalic acid and by-products of the production of dimethyl terephthalate are separated as solids.

4. A process according to claim 1, wherein the methanol is recovered from the mixture of water and methanol discharged from the first hydrolysis stage.

5. A process according to claim 1, wherein part of the mother liquor from the second hydrolysis stage is recycled into the first hydrolysis stage.

6. A process according to claim 1, wherein a portion of the suspension in the second hydrolysis stage is withdrawn and the solids proportion is partially or entirely dissolved by heating at 20° C. to 100° C., an expansion by pressure reduction is thereafter conducted, and the resultant suspension is recycled into a more dilute mother liquor passing upwardly through the second reactor column.

7. A process according to claim 1, wherein the mother liquor is expanded by pressure reduction only to such an extent that the dissolved terephthalic acid is precipitated and the by-products remain in solution; the thus-precipitated acid is separated from the liquid and recycled into the hydrolysis; the by-product-containing liquid phase, for separating the methanol, is separated by distillation into a methanol-water mixture discharged overhead and into an aqueous phase obtained in the sump at a sump temperature of between 200° and 300° C., said aqueous phase being further processed to eliminate by-products and to obtain residual amounts of terephthalic acid, and the thus-produced mother liquor is recycled into the process.

8. A process according to claim 1, wherein the crude dimethyl terephthalate is hydrolyzed with water at pressure of from 6 to 200 bars.

* * * * *